(12) United States Patent
Asami et al.

(10) Patent No.: US 9,074,512 B2
(45) Date of Patent: Jul. 7, 2015

(54) EXHAUST GAS ANALYZING SYSTEM AND EXHAUST GAS ANALYZING METHOD

(75) Inventors: Tetsuji Asami, Kyoto (JP); Hiroyuki Ikeda, Kyoto (JP); Mineyuki Komada, Kyoto (JP)

(73) Assignee: HORIBA, LTD., Kyoto (JP)

( * ) Notice: Subject to any disclaimer, the term of this patent is extended or adjusted under 35 U.S.C. 154(b) by 0 days.

(21) Appl. No.: 13/336,094

(22) Filed: Dec. 23, 2011

(65) Prior Publication Data

US 2012/0160009 A1     Jun. 28, 2012

(30) Foreign Application Priority Data

Dec. 27, 2010   (JP) ................. 2010-289654

(51) Int. Cl.
| | | |
|---|---|---|
| *G01N 7/00* | (2006.01) | |
| *F01N 11/00* | (2006.01) | |
| *G01N 1/22* | (2006.01) | |
| *F01N 13/00* | (2010.01) | |

(52) U.S. Cl.
CPC .............. *F01N 11/00* (2013.01); *G01N 1/2252* (2013.01); *F01N 2240/36* (2013.01); *Y02T 10/47* (2013.01); *F01N 13/009* (2014.06)

(58) Field of Classification Search
CPC ... F01N 13/009; F01N 11/00; F01N 2240/36; G01N 1/2252; Y02T 10/47
USPC .......... 73/23.31, 44, 55, 592, 514.07, 514.13, 73/23.2, 23.32
See application file for complete search history.

(56) References Cited

U.S. PATENT DOCUMENTS

| | | | |
|---|---|---|---|
| 3,957,372 A | | 5/1976 | Jowett et al. |
| 5,546,788 A | * | 8/1996 | Dickow ....................... 73/28.01 |
| 6,176,125 B1 | * | 1/2001 | Hirano et al. .............. 73/114.69 |
| 6,370,936 B1 | * | 4/2002 | Yamagishi et al. ............ 73/1.35 |
| 6,715,338 B1 | * | 4/2004 | Hsu ................................. 73/23.2 |

(Continued)

FOREIGN PATENT DOCUMENTS

| | | |
|---|---|---|
| CN | 101196435 A | 6/2008 |
| CN | 201149546 Y | 11/2008 |
| DE | 2557508 A | 7/1976 |

(Continued)

OTHER PUBLICATIONS

European Patent Office, European Search Report for European Patent Application No. EP11010203.5, dated Apr. 23, 2012, 6 pgs.

(Continued)

*Primary Examiner* — Peter Macchiarolo
*Assistant Examiner* — Mohammed Keramet-Amircola
(74) *Attorney, Agent, or Firm* — Brooks Kushman P.C.

(57) ABSTRACT

An exhaust gas analyzing system includes, on an upstream side of an analytical instrument, an exhaust gas introduction pipe of which one end is opened to an exhaust gas flow path through which exhaust gas from an engine flows and the other end is connected to the analytical instrument. A switching mechanism selectively switches between a sampling path that samples the exhaust gas from the exhaust gas introduction pipe to introduce the sampled exhaust gas into the analytical instrument and an air introduction path that introduces air into the analytical instrument. When the engine is operated, a path to the analytical instrument is switched to the sampling path by the switching mechanism. When the engine is stopped, the path is switched to the air introduction path by the switching mechanism.

4 Claims, 4 Drawing Sheets

(56) References Cited

U.S. PATENT DOCUMENTS

2001/0003915 A1* 6/2001 Inoue et al. .................. 73/23.2
2009/0151425 A1* 6/2009 Miwa .......................... 73/23.31

FOREIGN PATENT DOCUMENTS

| EP | 0668495 A2 | 8/1995 |
|---|---|---|
| JP | 61-084540 U | 6/1986 |
| JP | 61-247938 | 11/1986 |
| JP | 64-035344 | 2/1989 |
| JP | 2000-221123 | 8/2000 |
| JP | 2003130782 A | 5/2003 |
| JP | 2005-061913 | 3/2005 |
| JP | 2005507984 A | 3/2005 |
| JP | 2010-139281 | 6/2010 |
| JP | 2010139340 A | 6/2010 |

OTHER PUBLICATIONS

PHEV Measurement Challenges, AIGER Advisory Board Meeting, May 27, 2010, 19 pgs.
AIGER Homepage, Nov. 18, 2014, 2 pgs.
AIGER Project Briefing, May 27, 2010, 1 pg.
English translation of a decision of refusal for Japanese patent application JP2010-289654 dated Sep. 18, 2014, 12 pgs.

* cited by examiner

EXHAUST GAS ANALYZING SYSTEM AND EXHAUST GAS ANALYZING METHOD

CROSS-REFERENCE TO RELATED APPLICATION

This application claims priority to Japanese Patent Application No. 2010-289654 filed Dec. 27, 2010, the disclosure of which is incorporated in its entirety by reference herein.

TECHNICAL FIELD

The present invention relates to an exhaust gas analyzing system and an exhaust gas analyzing method that sample exhaust gas from an engine (internal combustion engine) to make an analysis.

BACKGROUND ART

In recent years, as the numbers of hybrid vehicles and idling stop vehicles increase, exhaust gas from a vehicle that stops an engine during driving tends to be measured.

As a conventional exhaust gas analyzer, as disclosed in Patent literature 1, there is one that directly samples exhaust gas from a tail pipe through which the exhaust gas from an engine flows, and introduces the sampled exhaust gas into an exhaust gas analyzer.

However, in the case of using the exhaust gas analyzer to measure exhaust gas of the above hybrid vehicle or the like, even if an engine is stopped, suction by a pump of the exhaust gas analyzer is applied. If so, inside the engine and a tail pipe, a gas flow that is different from a primary flow occurs, which may cause a problem, for example, a temperature of a catalyst provided in the tail pipe is changed, pressure of an exhaust port of the engine is reduced, or other problem.

At this time, it is thought that simultaneously with the engine stop, the pump of the exhaust gas analyzer is stopped to stop the measurement; however, in the case of stopping the pump, there occurs a problem that the gas suction is not instantaneously stopped due to inertia of the pump to create negative pressure inside pipes such as the engine and tail pipe, and thereby an engine condition is changed, a load is placed on the pump itself of the analyzer, or the gas unexpectedly flows, or other problem. Also, after the stop of the pump of the exhaust gas analyzer, if the pump is activated simultaneously with the start of the engine, a delay in rise of the pump or the like is of concern.

CITATION LIST

Patent Literature

Patent literature 1; JPA 2010-139340

SUMMARY OF INVENTION

Technical Problem

Therefore, the present invention has a main desired object to, in exhaust gas analysis of a vehicle that stops rotation of an engine during driving the vehicle, solve the problems due to the engine stop at once.

Solution to Problem

That is, an exhaust gas analyzing system according to the present invention is provided with, on an upstream side of an analytical instrument, an exhaust gas introduction pipe of which one end is opened to an exhaust gas flow path through which exhaust gas from an engine flows and the other end is connected to the analytical instrument, and a switching mechanism that selectively switches between a sampling path that samples the exhaust gas from the exhaust gas introduction pipe to introduce the sampled exhaust gas into the analytical instrument and an air introduction path that introduces air into the analytical instrument, wherein when the engine is operated, a path to the analytical instrument is switched to the sampling path by the switching mechanism, whereas when the engine is stopped, the path is switched to the air introduction path by the switching mechanism.

If so, when the engine is in an operating (rotating) state, the sampling path is established by the switching mechanism, whereas when the engine is stopped, the air introduction path is established, and therefore even if the analytical instrument remains operated when the engine is stopped, the gas is never sucked from the exhaust gas flow path to the exhaust gas introduction pipe. This enables problems such as an unexpected gas flow, catalyst temperature change, and pressure reduction of an exhaust port in the exhaust gas flow path at the time of engine stop to be solved. Also, even at the time of engine stop, it is not necessary to stop a pump of the analytical instrument, and therefore a problem due to a delay of a rise at the time of pump start or inertia at the time of pump stop can also be solved.

In order to not only simplify a configuration of the exhaust gas analyzing system and reduce cost to achieve a low price, but simplify an operation, preferably, the exhaust gas introduction pipe has: an upstream side pipe of which one end is opened to the exhaust gas flow path; and a downstream side pipe of which another end is connected to the analytical instrument, and the switching mechanism is a three way valve of which a first port is connected to the upstream side pipe, a second port is connected with the downstream side pipe, and a third port is opened to air.

Also, in order to automatically control the switching mechanism in accordance with the operation or stop of the engine, preferably, a control device that has received an engine operation related signal indicating whether or not the engine is in an operating state (operated) controls the switching mechanism.

Further, an exhaust gas analyzing method according to the present invention is provided with, on an upstream side of an analytical instrument, an exhaust gas introduction pipe of which one end is opened to an exhaust gas flow path through which exhaust gas from an engine flows and the other end is connected to the analytical instrument, and a switching mechanism that selectively switches between a sampling path that samples the exhaust gas from the exhaust gas introduction pipe to introduce the sampled exhaust gas into the analytical instrument and an air introduction path that introduces air into the analytical instrument, wherein when the engine is operated, a path to the analytical instrument is switched to the sampling path by the switching mechanism, whereas when the engine is stopped, the path is switched to the air introduction path by the switching mechanism.

Advantageous Effects of Invention

According to the present invention configured as described, problems such as an unexpected gas flow, catalyst temperature change, and pressure reduction of an exhaust port in the exhaust gas flow path at the time of engine stop can be solved. Also, it is not necessary to stop the pump of the analytical instrument, and therefore a problem due to a delay of a rise at the time of pump start or inertia at the time of pump stop can also be solved.

DESCRIPTION OF EMBODIMENTS

Figure 1:
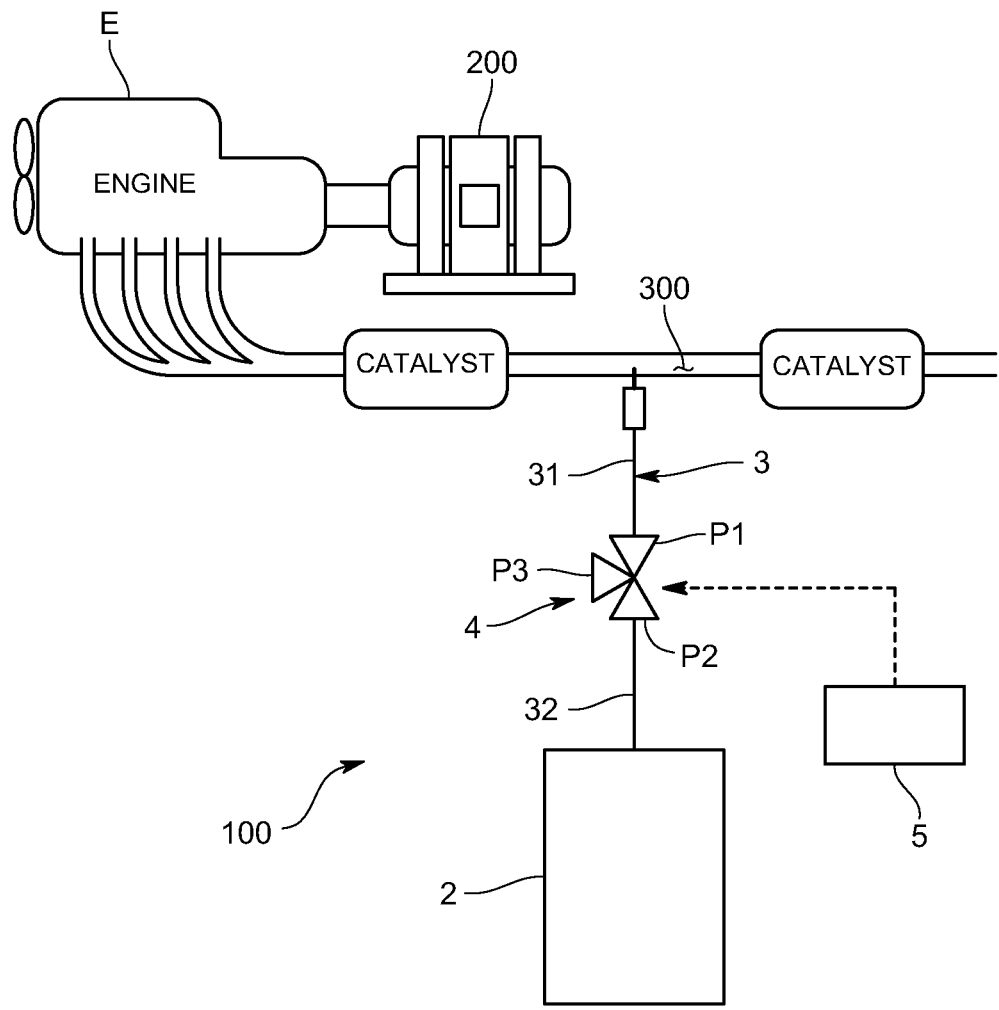
FIG. 1 is a diagram schematically illustrating a configuration of an exhaust gas analyzing system of the present embodiment.

In the following, one embodiment of an exhaust gas analyzing system according to the present invention is described referring to the drawings.

An exhaust gas analyzing system 100 according to the present embodiment is one that analyzes exhaust gas from an engine attached to an engine dynamo 200.

Specifically, the exhaust gas analyzing system 100 is provided with: an exhaust gas analyzer 2 serving as an analytical instrument that analyzes the exhaust gas from the engine E; an exhaust gas introduction pipe 3 of which one end is opened to an exhaust gas flow path through which the exhaust gas from the engine E attached to the engine dynamo 200 flows and the other end is connected to the exhaust gas analyzer 2; a switching mechanism 4 that is provided in the exhaust gas introduction pipe 3 and selectively switches between a sampling path L1 that samples the exhaust gas from the exhaust gas introduction pipe 3 and an air introduction path L2 that introduces air; and a control device 5 that controls the switching mechanism 4. Note that the exhaust gas introduction pipe 3, the switching mechanism 4, and the control device 5 constitute an exhaust gas sampling device.

The exhaust gas analyzer 2 is one that measures concentrations of measurement components contained in the exhaust gas, and measures concentrations of, for example, CO and $CO_2$ by an NDIR method, THC by an FID method, and $NO_x$ by a CLD method.

Also, in the exhaust gas flow path 300, on upstream and downstream sides with respect to the one end opening of the exhaust gas introduction pipe 3, exhaust gas purification catalysts for purifying the exhaust gas are respectively provided.

The switching mechanism 4 of the present embodiment is configured to have a three way solenoid valve that is provided in the exhaust gas introduction pipe 3. The three way solenoid valve 4 has: an upstream side port (first port) P1 that is connected with an upstream side pipe 31 constituting the exhaust gas introduction pipe 3; a downstream side port (second port) P2 that is connected with a downstream side pipe 32 constituting the exhaust gas introduction pipe 3; and an air opening port (third port) P3 that is opened to air. In addition, an upstream side opening of the upstream side pipe 31 is opened into the exhaust gas flow path 300. Also, a downstream side of the downstream side pipe 32 is connected to a gas introduction port of the exhaust gas analyzer 2. In addition, the air opening port P3 may be connected with a pipe that is opened to air.

Figure 2:
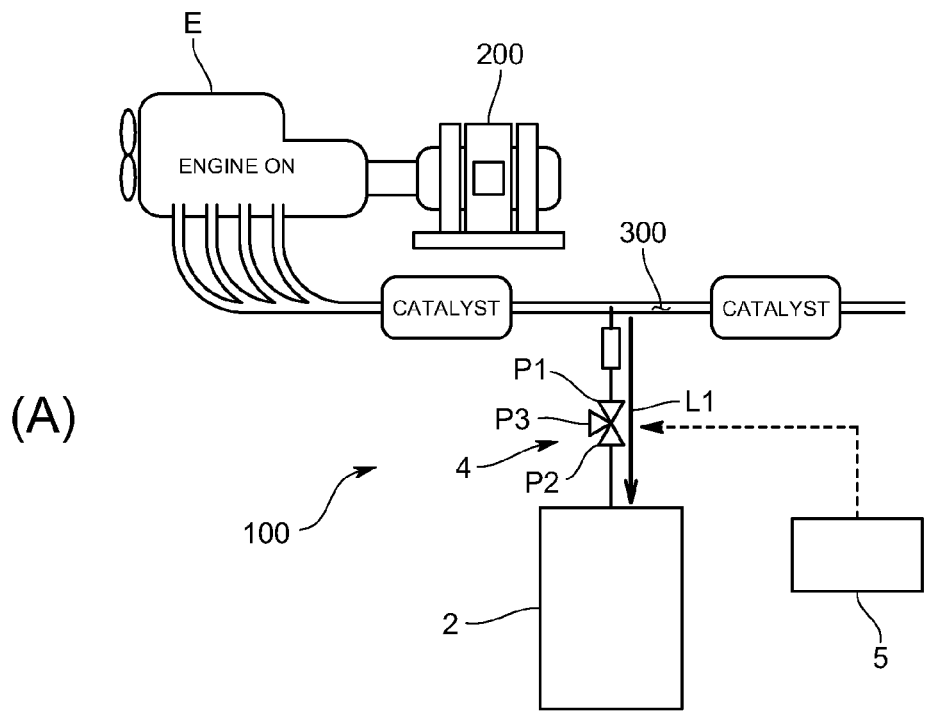
FIG. 2 is a diagram illustrating a sampling path and air introduction path in the same embodiment.
Figure 2:
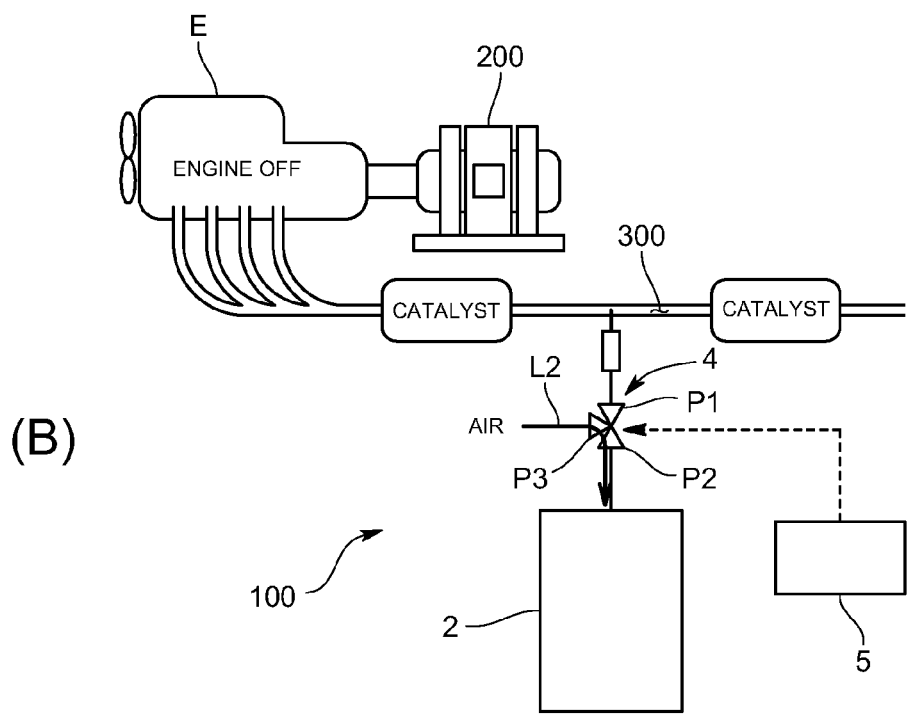

The three way solenoid valve 4 is controlled by the aftermentioned control device 5, and as illustrated in FIG. 2, selectively switches between the sampling path L1 (see FIG. 2 (A)) that communicatively connects the upstream side port P1 and downstream side port P2 with each other and the air introduction path L2 (see FIG. 2 (B)) that communicatively connects the air opening port P3 and downstream side port P2 with each other. In order to enhance switching responsiveness, the three way solenoid valve 4 is preferably close to a sampling point, and in the present embodiment, provided in the exhaust gas introduction pipe 3 near outside a pipe forming the exhaust gas flow path 300.

The control device 5 is a dedicated or general-purpose computer that is provided with a CPU, a memory, an I/O channel, an A/D converter, and the like, and according to a control program stored in the memory, the CPU and its peripheral devices cooperatively works to thereby switch the three way solenoid valve 4 serving as the switching mechanism in accordance with operation/stop of the engine E.

Specifically, when the engine E is in an operating state, the control device 5 controls the three way solenoid valve 4 to thereby establish the sampling path L1, whereas when the engine E is stopped, the control device 5 controls the three way solenoid valve 4 to thereby establish the air introduction path L2. On the basis of this, when the engine E is operated (rotated), a sample is introduced into the exhaust gas analyzer 2, whereas when the engine E is stopped, air is introduced into the exhaust gas analyzer 2.

The control device 5 performs the switching control of the three way solenoid valve 4 on the basis of an engine operation related signal obtained from the engine E or a peripheral device of the engine E. The engine operation related signal is a signal indicating whether or not the internal combustion engine is in the operating state, i.e., the engine E is rotated (operation (ON)/stop (OFF) of the engine E), and for example, a detection signal obtained from a pickup sensor that detects a rotation number of the engine E, an ignition signal of the engine E, an engine rotation number signal obtained by analyzing vibration or noise of the engine E, an engine rotation number signal obtained from the engine dynamo 200 serving as a peripheral device, an exhaust gas flow rate signal obtained from a flow rate sensor that detects a flow rate of the exhaust gas that flows through the exhaust gas flow path 300, an intake air flow rate signal obtained from a flow rate sensor that detects an intake air flow rate of the engine E, or other signal.

The control device 5 obtains the above engine operation related signal to determine whether or not the engine E is being rotated (ON/OFF of the engine E), and if determining that the engine E is OFF, switches the three way solenoid valve 4 to establish the air introduction path L2. On the other hand, if determining that the engine E is ON, the control device 5 switches the three way solenoid valve 4 to establish the sampling path L1.

Note that in the case of using any of the above signals as the engine operation related signal, switching timing may be delayed relative to actual engine operation. In such a case, as the engine operation related signal, an engine starting signal may be alternatively used. Alternatively, for example, in the case where as with an idling stop vehicle, ON/OFF of the engine E is clearly distinguished in a test mode interval, by using, as the engine operation related signal, an analysis signal obtained by analyzing a test mode, the switching mechanism 4 can also be switched at timing to switch ON/OFF the engine E to thereby switch between the sampling path L1 and the air introduction path L2.

According to the exhaust gas analyzing system 100 according to the present embodiment configured as described, the three way solenoid valve 4 establishes the sampling path L1 when the engine is operated, whereas when the engine is stopped, it establishes the air introduction path L2, and therefore even in the case where the exhaust gas analyzer 2 remains operated, the gas is never sucked from the exhaust gas flow path 300 to the exhaust gas introduction pipe 3 when the engine is stopped. This enables the problems such as an unexpected gas flow, catalyst temperature change, and pressure reduction of an exhaust port in the exhaust gas flow path 300 at the time of engine stop to be solved.

Also, even at the time of engine stop, it is not necessary to stop the pump of the exhaust gas analyzer 2, and therefore the problem due to a delay of the rise at the time of pump start or the inertia at the time of pump stop can also be solved.

Further, the use of the three way solenoid valve 4 enables not only a configuration of the exhaust gas analyzer 100 to be simplified and cost to be reduced to achieve a low price but an operation to be simplified.

In addition, by providing the three way solenoid valve 4, in the case like a warm up mode in which the exhaust gas is not sampled, gas can be flowed back from the exhaust gas analyzer 2 side to purge the exhaust gas introduction pipe 3. Also, even in the situation where in the case of making long time measurements, purging is required along the way, the purging can be performed without influencing the engine E side.

Note that the present invention is not limited to the above-described embodiment.

In the case of stopping or starting the measurement in accordance with the stop or operation of the engine, corresponding timing is important. In the case of the exhaust gas analyzing system 100 that performs exhaust gas sampling, a delay time caused by the exhaust gas that flows from the sampling point to the analytical instrument 2 is also important for improving accuracy of exhaust amount calculation. The delay time is different depending on the type of the analytical instrument 2 or a pipe length, and therefore it is preferable to measure a delay time for each component to correct the delay time at the time of calculating the exhaust amount.

In order to measure the delay time, for example, standard gas of which component concentrations are known, or the like, is supplied to the upstream side opening of the exhaust gas introduction pipe, and a gas flow path is switched to the sampling path by the switching mechanism. By comparing timing of the switching with rise timing of an indication of the analytical instrument, a delay time at the time of measurement start is known. Similarly, in a state where the standard gas of which the concentrations are known, or the like, is flowed, the gas flow path is switched to the air introduction path by the switching mechanism. By comparing timing of the switching with a fall timing of the indication of the analytical instrument, a delay time at the time of measurement stop is known. Note that without separately providing a supply mechanism that supplies the standard gas of which the component concentrations are known, by bringing the engine into a steady state to make an exhaust gas concentration constant, a similar delay time can be measured.

Also, in the above-described embodiment, the switching mechanism 4 is the three way solenoid valve, and the control device 5 obtains the engine operation related signal to automatically switch the three way solenoid valve 4; however, a user may operate the control device 5 to thereby switch the three way solenoid valve 4.

Also, the present invention may be configured such that the switching mechanism 4 is configured to have a three way valve and a user manually switches the three way valve.

Further, the exhaust gas analyzing system of the above-described embodiment employs the exhaust gas analyzer 2 as an analytical instrument; however, the exhaust gas analyzing system may employ a PM analyzer instead.

Figure 3:
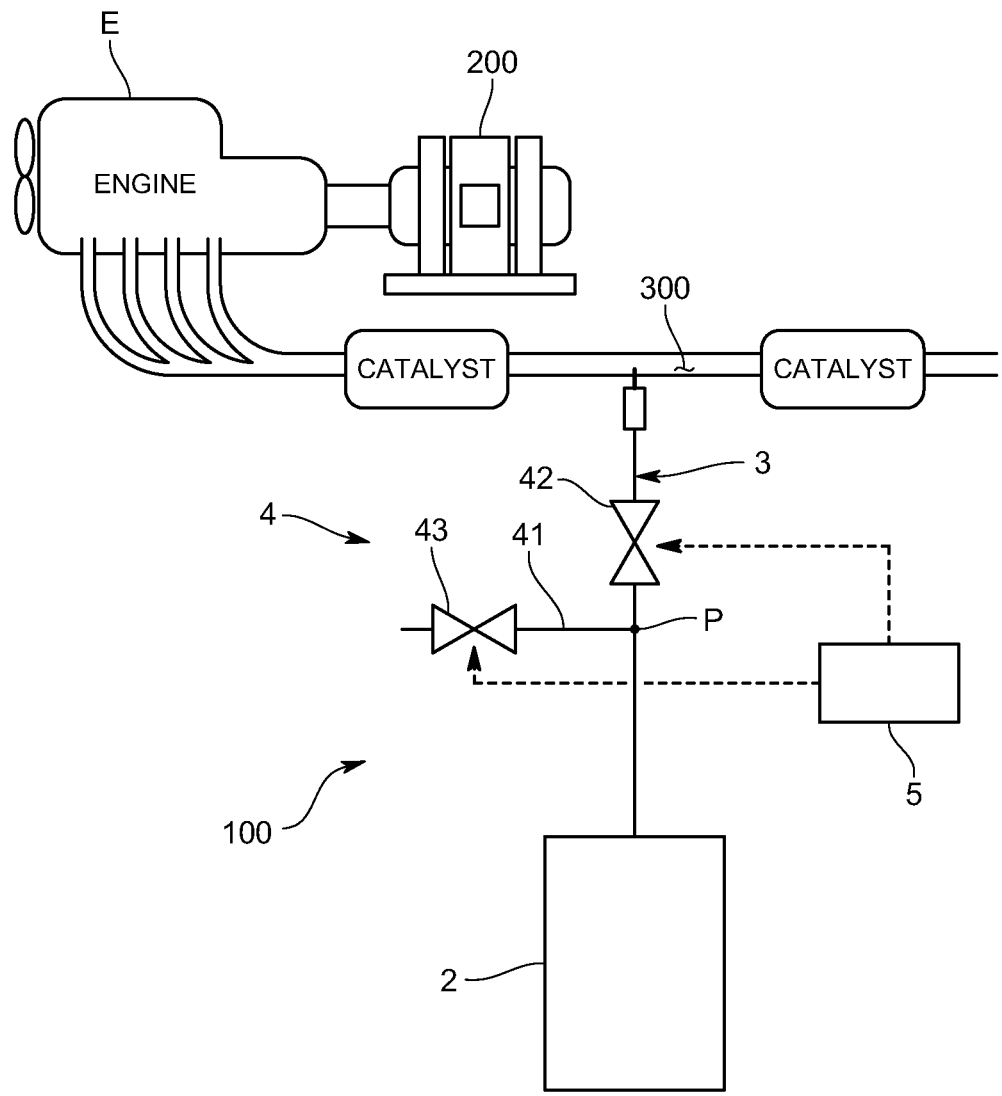
FIG. 3 is a diagram illustrating a switching mechanism according to a variation.

Besides, the present invention may be configured such that as the switching mechanism 4, as illustrated in FIG. 3, an air opening pipe 41 that is branched from the exhaust gas introduction pipe 3 is provided, and on upstream sides of a point of the branch P, on/off valves 42 and 43 are respectively provided.

Figure 4:
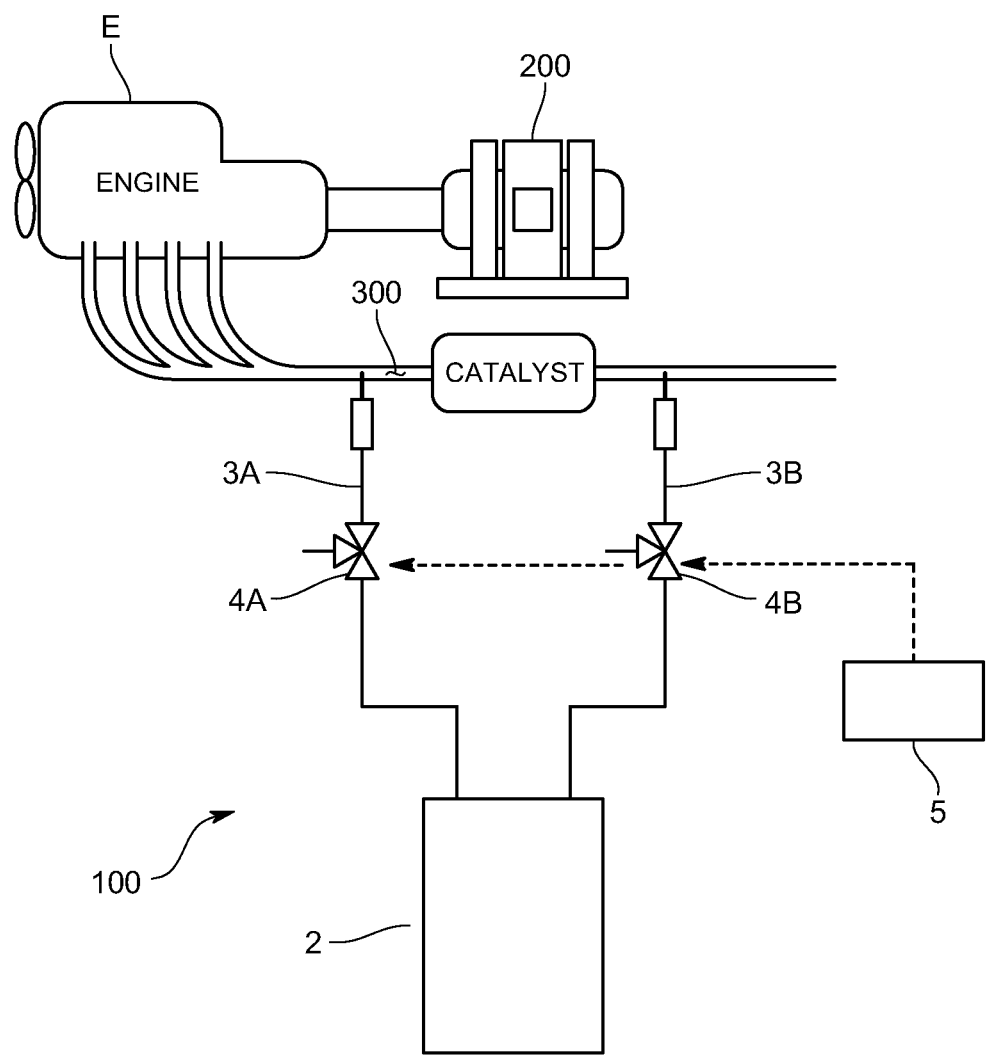
FIG. 4 is a diagram schematically illustrating a configuration of another exhaust gas analyzing system.

In addition, the present invention may be adapted to use the exhaust gas analyzing system 100 to sample exhaust gas from each of upstream and downstream sides of an exhaust gas purification catalyst provided on the exhaust gas flow path 300, and analyze the sampled exhaust gas to thereby analyze purification efficiency of the catalyst. In this case, the exhaust gas analyzing system 100 is, as illustrated in FIG. 4, provided with: a first exhaust gas introduction pipe 3A that samples exhaust gas from the upstream side of the exhaust gas purification catalyst; and a second exhaust gas introduction pipe 3B that samples exhaust gas from the downstream side of the exhaust gas purification catalyst, and each of the first and second exhaust gas introduction pipes 3A and 3B is provided with a switching mechanism 4A or 4B that selectively switches between a sampling path L1 and an air introduction path L2.

Besides, it should be appreciated that the present invention is not limited to any of the above-described embodiments, but can be variously modified without departing from the scope thereof.

REFERENCE SIGNS LIST

100: Exhaust Gas Analyzing System
300: Exhaust Gas Flow Path
2: Exhaust Gas Analyzer (analytical instrument)
3: Exhaust Gas Introduction Pipe
L1: Sampling path
L2: Air Introduction Path
4: Switching Mechanism (three way solenoid valve)
5: Control Device

The invention claimed is:

1. An exhaust gas analyzing system comprising:
an analytical instrument that analyzes exhaust gas from an engine and that is provided separately from an exhaust gas flow path through which the exhaust gas from the engine flows;
an exhaust gas introduction pipe of which one end is opened to the exhaust gas flow path and the other end is connected to the analytical instrument;
a pump that samples the exhaust gas flowing through the exhaust gas flow path by the exhaust gas introduction pipe to introduce it into the analytical instrument and that operates during an exhaust gas measurement without stopping while the engine is switched between stopped and operating states, and
a switching mechanism that selectively switches between a sampling path that samples the exhaust gas from the exhaust gas flow path by the pump operating without stopping during the exhaust gas measurement to introduce the sampled exhaust gas into the analytical instrument from the exhaust gas introduction pipe and an air introduction path that introduces air into the analytical instrument by the pump while the sampling path to the analytical instrument is cut off,
wherein when the engine switches from the stopped state to the operating state while the pump is operating without stopping during the exhaust gas measurement, a path to the analytical instrument is switched to the sampling path by the switching mechanism and wherein when the engine switches from the operating state to the stopped state while the pump is operating without stopping during the exhaust gas measurement, the sampling path to the analytical instrument is cut off by the switching mechanism and the path is switched to the air introduction path by the switching mechanism.

2. The exhaust gas analyzing system according to claim 1, wherein the exhaust gas introduction pipe has: an upstream side pipe of which one end is opened to the exhaust gas flow path; and a downstream side pipe of which another end is connected to the analytical instrument, and the switching mechanism is a three way valve of which a first port is connected to the upstream side pipe, a second port is connected with the downstream side pipe, and a third port is opened to air.

3. The exhaust gas analyzing system according to claim 1, wherein a control device that has received an engine operation related signal indicating whether or not the engine is in an operating state controls the switching mechanism.

4. An exhaust gas analyzing method using an exhaust gas analyzing system including an analytical instrument that analyzes exhaust gas from an engine and that is provided separately from an exhaust gas flow path through which the exhaust gas from the engine flows, an exhaust gas introduction pipe of which one end is opened to the exhaust gas flow path and the other end is connected to the analytical instrument, a pump that samples the exhaust gas flowing through the exhaust gas flow path by the exhaust gas introduction pipe to introduce it into the analytical instrument and that operates during an exhaust gas measurement without stopping while the engine is switched between stopped and operating states, and a switching mechanism that selectively switches between a sampling path that samples the exhaust gas from the exhaust gas flow path by the pump operating without stopping during the exhaust gas measurement to introduce the sampled exhaust gas into the analytical instrument from the exhaust gas introduction pipe and an air introduction path that introduces air into the analytical instrument by the pump while the sampling path to the analytical instrument is cut off, the method comprising:

when the engine switches from the stopped state to the operating state while the pump is operating without stopping during the exhaust gas measurement, a path to the analytical instrument is switched to the sampling path by the switching mechanism, and when the engine switches from the operating state to the stopped state while the pump is operating without stopping during the exhaust gas measurement, the sampling path to the analytical instrument is cut off by the switching mechanism and the path is switched to the air introduction path by the switching mechanism.

\* \* \* \* \*